(12) United States Patent
Behkish et al.

(10) Patent No.: US 12,152,268 B2
(45) Date of Patent: Nov. 26, 2024

(54) BIOLOGICAL GUARD BEDS IN CONVERSION OF BIOMASS INTO HYDROCARBON FUELS AND CHEMICALS

(71) Applicant: ExxonMobil Technology and Engineering Company, Annandale, NJ (US)

(72) Inventors: Arsam Behkish, Flemington, NJ (US); Giovanni Pilloni, Jersey City, NJ (US); Changyub Paek, Bridgewater, NJ (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 0 days.

(21) Appl. No.: 16/870,916

(22) Filed: May 9, 2020

(65) Prior Publication Data

US 2021/0017549 A1   Jan. 21, 2021

Related U.S. Application Data

(60) Provisional application No. 62/876,007, filed on Jul. 19, 2019.

(51) Int. Cl.
*C12P 7/10*  (2006.01)
*C12M 1/00*  (2006.01)
*C12P 7/649*  (2022.01)

(52) U.S. Cl.
CPC ............ *C12P 7/10* (2013.01); *C12M 43/02* (2013.01); *C12M 45/06* (2013.01); *C12P 7/649* (2013.01); *C12P 2201/00* (2013.01)

(58) Field of Classification Search
CPC ......... C12P 7/10; C12P 2201/00; C12P 7/649; C12M 43/02; C12M 45/06
USPC ........................................ 435/165
See application file for complete search history.

(56) References Cited

U.S. PATENT DOCUMENTS

| | | | | |
|---|---|---|---|---|
| 2011/0003352 A1* | 1/2011 | Retsina | ..................... | C08H 8/00 |
| | | | | 435/136 |
| 2015/0118736 A1* | 4/2015 | Wu | .......................... | C12N 1/22 |
| | | | | 435/276 |
| 2017/0002387 A1* | 1/2017 | Retsina | ..................... | C08H 8/00 |

FOREIGN PATENT DOCUMENTS

WO   WO 2015/026660   *   2/2015   ................ C12P 7/10

OTHER PUBLICATIONS

Wierckx et al., Isolation and characterization of Cupriavidus basilensis HMF14 for biological removal of inhibitors from lignocellulosic hydrolysate, Microbial Biotechnology, 3(3), (2010), pp. 336-343.*

(Continued)

*Primary Examiner* — Jennifer M. H. Tichy
(74) *Attorney, Agent, or Firm* — Shook, Hardy & Bacon L.L.P.

(57) ABSTRACT

The present disclosure relates to processes for producing hydrocarbon fuels from lignocellulosic biomass. A process may include introducing biomass to a pretreatment system forming a pretreatment effluent and introducing the pretreatment effluent to a hydrolysis system forming a hydrolysate. The hydrolysate may be introduced to a lignin separation system to form a sugar-rich stream and a lignin-rich stream. The sugar-rich stream may be introduced to a purification system comprising at least one toxin converting microorganism or subcellular material to form a purified sugar-rich stream, and the purified sugar-rich stream and one or more sugar converting microorganisms are introduced to a bioreactor configured to produce hydrocarbon fuels. Additionally, the present disclosure also related to systems for production of hydrocarbon fuels including, a pretreatment system, a hydrolysis system, a lignin separation system, a purification system, and at least one bioreactor.

20 Claims, 3 Drawing Sheets

(56) References Cited

OTHER PUBLICATIONS

Steen et al., Microbial production of fatty-acid derived fuels and chemicals from plant biomass, Nature, Letters, vol. 463, (Jan. 28, 2010), pp. 559-563.*

Erdei et al., "Separate hydrolysis and co-fermentation for improved xylose utilization in integrated ethanol production from wheat meal and wheat straw", Biotechnology for Biofuels (2012), vol. 5, No. 12, pp. 1-13.

Nielsen et al., "Sequential targeting of xylose and glucose conversion in fed-bath simultaneous saccharification and co-fermentation of steam-pretreated wheat straw for improved xylose conversion to ethanol", Bioenergy. Res. (2017), vol. 10, pp. 800-810.

Nielsen et al., "Prefermentation improves ethanol yield in separate hydrolysis and confermentation of steam- pretreated wheat straw", Sustainable Chemical Processes (2016), vol. 4, No. 10, pp. 1-12.

Davis et al., "Process Design and Economics for the Conversion of Lignocellulosic Biomass to Hydrocarbons:Dilute- Acid and Enzymatic Deconstruction of Biomass to Sugars and Biological Conversion of Sugars to Hydrocarbons", Technical Report NREL/TP-5100-60223, Oct. 2013.

Kumar et al., "Recent updates on different methods of pretreatment of lignocellulosic feedstocks: a review", Bioresources and Bioprocessing (2017), vol. 4, No. 7, pp. 1-19.

Jonsson et al., "Pretreatment of lignocellulose: Formation of inhibitory by-products and strategies for minimizing their effects", Bioresource Technology, (2016), vol. 199, pp. 103-112.

Weil et al., "Removal of Fermentation Inhibitors Formed during Pretreatment of Biomass by Polymeric Adsorbents", Ind. Eng. Chem. Res. (2002), vol. 41, No. 24, pp. 6132-6138.

Jonsson et al., "Bioconversion of lignocellulose: inhibitors and detoxification", Biotechnology for Biofuels (2013), vol. 6, No. 16, pp. 1-10.

Nichols et al., "Bioabatement to Remove Inhibitors from Biomass-Derived Sugar Hydrolysates", Applied Biochemistry and Biotechnology (2005), vol. 121 - 124, pp. 379-390.

* cited by examiner

BIOLOGICAL GUARD BEDS IN CONVERSION OF BIOMASS INTO HYDROCARBON FUELS AND CHEMICALS

CROSS-REFERENCE TO RELATED APPLICATIONS

This application claims priority to U.S. Provisional Application No. 62/876,007 filed Jul. 19, 2019, which is herein incorporated by reference in its entirety.

FIELD OF THE INVENTION

The present disclosure relates to methods and systems for converting biomass into hydrocarbon fuels and chemicals and, in particular, to methods and systems for converting biomass including lignocellulosic material into sugars and purifying them using microorganisms to before bioconversion of the purified monosaccharide sugars into hydrocarbon fuels and chemicals.

BACKGROUND OF THE INVENTION

Global efforts are underway for the development of sustainable sources of energy, including biofuels and biochemicals, to reduce reliance on fossil fuels and reduce greenhouse gas emissions. For example, the United States, through the Energy Independence and Security Act (EISA) of 2007 and subsequently the expanded Renewable Fuel Standard (RFS) program, aims to increase the production of renewable fuel, by increasing amounts each year relative to petroleum-based fuels. Accordingly, the development of renewable or sustainable energy is of particular interest.

The use of biomass for making sustainable energy has been a focus for achieving reduced greenhouse gas emissions. The Renewable Fuel Standard targets are set to reduce emissions based on feedstock source of the biofuel. Much of the efforts to produce sustainable energy and biofuels have focused food-related biomass and conversion into light alcohols, such as ethanol. For example, ethanol has been derived from sugarcane, chemically transesterified vegetable oils, seed oils, or animal fats. A primary source of food-related biomass currently used for producing sustainable energy is derived from corn (e.g., corn starch). However, such food-related biomasses, such as corn, are major global food sources and, accordingly, these efforts for producing sustainable energy compete with food availability. Furthermore, the reduction in greenhouse gas emissions associated with biofuels developed from food-related biomass is dampened primarily due to the uncertainty associated with land use change. For example, the use of food-related biomass for fuels may require greater quantities of land (and increase deforestation) to produce both food for consumption and food-related biomass to be converted into biofuels.

As a result, new efforts, including mandates from the Renewable Fuel Standard program, have been focused on biofuels derived from non-food biomass to meet the demand for sustainable energy without competing with food resources. These non-food biomass sources include, for example, residues from agriculture, forestry, and municipal solid waste. It is estimated that sustainable energy from non-food biomass could satisfy a sizable percentage of the transportation fuel and diesel demands in the near future, thereby decreasing reliance on fossil fuels. Furthermore, the potential to reduce greenhouse gas emissions is greater because there is reduced or eliminated demand for changes in the use of land. For example, the use of biomass arising from residues from agriculture, forestry, and municipal solid waste requires little or no change in the use of land for production of food and fuels.

One source of biomass that has been of interest is non-food biomass including lignocellulose material. Lignocellulose is present in all plant biomass, and is a complex of lignin, hemicellulose, and cellulose present in plant cell walls. Such lignocellulosic material, including those derived from agricultural waste, forest residue, and energy crops, is readily available and does not compete with food resources to supply fermentable sugars that can be harnessed to produced biofuels and biochemicals.

Fermentable sugars may be converted to fatty acid esters by sugar converting (SC) microorganisms, including genetically modified SC microorganisms. The bioconversion to fuels and chemicals may be accomplished in fed-batch reactors, which are reactors in which a culture of certain SC microorganisms is fed and typically, in which the product remains until the end of the reactor run. The production of fatty acid esters (hydrocarbon fuels) from lignocellulosic materials in fed-batch bioreactors remains of interest in reduction of reliance on fossil fuels and reduction of production of greenhouse gases.

However, conversion of lignocellulosic biomass into fermentable sugars produces byproducts that may negatively affect the conversion of the sugars into fuels and chemicals. Toxins and inhibitors, such as carboxylic acids and furan compounds, released from the conversion of lignocellulosic biomass to sugars may be harmful to SC microorganisms or may inhibit the conversion of sugars to fuels and chemicals. Some SC microorganisms are sensitive to even ppm levels of toxins and, as a result, the conversion of sugar and the yield and selectivity of the reaction are reduced. While there are methods that may remove a portion of toxins and inhibitors from the feed stream, because such methods do not fully remove all the toxins or inhibitors a portion of the toxins and/or inhibitors remain in the feed stream to the bioreactors. Further removal of toxins or inhibitors has involved more complicated processes and operating conditions that deviate significantly from the main process conditions, hence adding to the initial cost and operating costs of producing biofuels from sugars at a biorefinery. Additionally, purification may result in loss of a portion of the fermentable sugars derived from biomass decreasing the efficiency of the overall process.

Considerable effort has been put into the genetic modification of SC microorganisms to increase resistance to byproducts from the production of sugars from lignocellulosic materials. Resistance based on genetic modification may decrease metabolic efficiency because for each new genetic feature, the added metabolic pathway typically needs cellular energy, such as ATP, to operate. Ultimately, cellular energy depends on the supply of nutrients provided to the bioreactor and is therefore limited either by the rate of feed to the reactor or by a limited time on stream as a fed-batch reactor fills to capacity. Therefore, the process of coping with inhibitory compounds may compete with other conversion processes using cellular energy, including the bioconversion of sugars into fuels and chemicals, hence affecting the yield and selectivity.

Production of fermentable sugars may include concentration of various sugar streams, but the concentration of sugars may also increase the concentration of inhibitors and toxins, often time to levels which are well above the threshold of toxicity for the SC microorganism in the bioreactor. Therefore, purification may improve the efficiency of processes and systems for bioconversion of sugars produced from lignocellulosic biomass. Several purification methods may be employed including chemical reducing agents, or absorption beds (also called resin beds). These techniques may have efficient removal of toxins, but are frequently limited by adsorption capacity, reactor size, or operating conditions. The previous purification methods typically leave some low level of toxins in the purified and concentrated sugar feed stream to the bioreactor. Since the bioreactors are generally operated in the fed-batch mode, the level of these toxins, albeit low, can and will accumulate in the reactor over the entire length of the run, and hence reach a level that is ultimately harmful to the SC microorganism and interrupt (abruptly) the reaction. Furthermore, even low levels of certain byproducts may inhibit the bioconversion process. Additionally, adsorption beds may be limited in the number or type of toxins they can remove, therefore several adsorption beds designed for different materials may be included in order to treat a variety of byproducts. Furthermore, adsorption beds require replacement or regeneration (which is typically energy intensive). This added complexity, and cost associated with it, may increase if the biomass feedstock is switched since the type, number, and level of toxins could change as a result of the different biomass source. Therefore, the design and operation may include a high degree of flexibility to accommodate for various toxins and inhibitors that may potentially be present in the feed stream. One disadvantage of such complexity is that there is sugar loss due to the number and size of adsorption beds used to remove sufficient toxins and inhibitors from the sugar streams. Overall the process economics will suffer as a consequence.

There is a need for improved and more versatile removal of toxins and inhibitors in the production of fuels and/or other chemicals from lignocellulosic biomass. Additionally, there is a need for methods and systems with simple design and easy, but flexible operation that are capable of reducing or eliminating the toxins and inhibitors without a concurrent loss of sugars.

SUMMARY

The present disclosure relates to processes for producing hydrocarbon fuels from lignocellulosic biomass. A process may include introducing biomass to a pretreatment system forming a pretreatment effluent and introducing the pretreatment effluent to a hydrolysis system forming a hydrolysate. The hydrolysate may be introduced to a lignin separation system to form a sugar-rich stream and a lignin-rich stream. The sugar-rich stream may be introduced to a purification system comprising at least one toxin converting microorganism or subcellular material to form a purified sugar-rich stream, and the purified sugar-rich stream and one or more sugar converting microorganisms are introduced to a bioreactor configured to produce hydrocarbon fuels.

Furthermore, a process for producing hydrocarbon fuels from lignocellulosic biomass may include introducing the pretreatment effluent to a purification system before hydrolysis to form the hydrolysate.

The present disclosure also related to systems for production of hydrocarbon fuels including, a pretreatment system, a hydrolysis system, a lignin separation system, a purification system, and at least one bioreactor.

DETAILED DESCRIPTION

Global demands motivate the development of sustainable energy sources, such as biofuels and biochemicals, which can decrease greenhouse gas emissions, decrease reliance on fossil fuels, and, ideally, do not compete with food sources. Lignocellulosic material (also referred to as lignocellulosic biomass) may be used to satisfy the global demand for sustainable energy. Furthermore, lignocellulosic biomass is readily available and may be derived from agricultural residue and waste, forest residue, and energy crops. Bioconversion processes that convert lignocellulosic biomass, especially at commercial scales, have the potential to greatly reduce greenhouse gas emissions without competing with important food resources.

The methods and systems described provide for a biological conversion of sugars obtained from lignocellulosic biomass using SC microorganisms, such as genetically modified *Escherichia coli* (*E. coli*), a naturally occurring SC microorganism found in healthy human intestines. In particular, the methods and systems described provide for conversion of sugars into fuels and chemicals, such as fatty acid methyl ester (FAME). Moreover, the methods and systems described can utilize a variety of biomass material feeds for conversion of lignocellulosic compounds, and permit production of a variety of distillate products, further enhancing commercial scalability. Additionally, unlike production of biodiesel from vegetable oil, the processes and systems using lignocellulosic feedstock do not directly compete with food production.

In some embodiments, the present disclosure provides for a method and system that converts lignocellulosic material derived from one or more biomass sources into its primary components of hemicellulose, cellulose, and lignin. The amount of each of these primary components is specific to the type of biomass, for example, corn stover and wheat straw contain different mixtures of hemicellulose, cellulose, and lignin. The lignin is separated from the hydrolyzed material and may be burnt in a steam generator (e.g., a boiler), for example, to produce energy, such as steam and/or electricity. The hemicellulose and cellulose are further hydrolyzed to release monosaccharides for bioconversion. However, the breakdown of hemicellulose also produces byproducts such as organic acids and furan compounds which may be toxic to the SC microorganisms or inhibit the processes that convert sugars into fuels and chemicals.

It has been discovered that removal of toxins and inhibitors may be accomplished by the addition of biological guard bed(s), which may be a bioreactor containing toxin converting (TC) microorganisms, as wild type or genetically modified, or subcellular components of TC microorganisms designed to convert or digest toxins and inhibitors into compounds that are not toxic or not inhibitory to the SC microorganisms that convert sugars to fuels and chemicals, without consuming or converting much (if any) of the fermentable sugars produced from the biomass. For example, the toxins and inhibitors may be converted to water, carbon dioxide, and/or hydrogen. In this manner the conversion of sugar to hydrocarbon fuels can have improved efficiency and the processes can be enhanced, because in the production of fuels or other chemicals, SC microorganism energy would not need to be diverted to detoxification processes.

Additionally, the removal of toxins from the sugar feed stream using TC microorganisms or subcellular components allows for sugar to be obtained from different lignocellulosic biomass sources where different types of toxins and inhibitors in varying degree of concentration may be released. Therefore, the biological guard bed(s) may reduce the complexity of sugar cleanup process(es), including a robust and versatile design in order to remove potential toxins and inhibitors that can be present in various lignocellulosic biomass feeds. Because the biological guard bed may adapt to different toxins at various concentrations, the use of biological guard beds may overcome many of the failings of prior processes and systems.

Furthermore, design and development of SC microorganisms for bioconversion of biomass to fuels and chemicals typically includes significant research and development costs and effort. The costs of design and development may be reduced by improving the sugar feeds to the SC microorganism by improving the removal of toxins and inhibitors. Additionally, with sufficient removal of byproducts and toxins in a feed stream the development of the SC microorganisms does not need to include toxin resistance, making the development easier and the SC microorganisms more efficient. Therefore, the reduction or elimination of toxins and inhibitors improves the efficiency of bioconversion processes, accelerates the design and development of the SC microorganism, and reduces time to commercial deployment.

It has further been discovered that biological guard beds may more efficiently remove various toxins and inhibitors over previous processes. A biological guard bed may replace multiple adsorption beds, simplifying the purification processes. The simplification of purification processes leads to a decrease in many different costs, including costs related to building a biorefinery, maintaining systems, regenerating adsorption beds, or design and development of SC microorganisms for bioconversion processes. Furthermore, the TC microorganisms or subcellular materials in a biological guard bed may have reduced sugar loss compared to previous purification processes. Additionally, the use of TC microorganisms or subcellular materials in a biological guard bed may allow for greater sugar production because the pretreatment conditions may be altered outside of current practices. Currently, pretreatment conditions are tightly regulated so as not to release as many toxins, but if toxins are more efficiently removed the pretreatment conditions may be altered to improve deconstruction of the biomass over current processes.

Furthermore, the use of biological guard beds might not be as limited in types of toxins and inhibitors removed as with previous purification processes, and use of biological guard beds may have increased flexibility on the types of biomass feeds that may be used. Therefore, the use of a biological guard bed may yield a significant improvement in the overall performance and economics of the processes and systems used in bioconversion of biomass to fuels and other chemicals.

Definitions

The terms "lignocellulosic material," "lignocellulosic biomass," "lignocellulose," and grammatical variants thereof, are used interchangeably and are broad terms including a complex of namely hemicellulose, cellulose, and lignin present in the cell walls of woody plants. "Lignocellulosic feedstock," and grammatical variants thereof, includes biomass materials that include lignocellulosic material including, agricultural residues and waste (e.g., corn stover, wheat straw, bagasse), forest residues (e.g., woodchips), energy crops (e.g., switch grass, wheatgrass, bamboo), or combination(s) thereof.

The term "biomass" and grammatical variants thereof, refers to biological, organic matter that can be converted to fuel. The biomass for use in the embodiments of the present disclosure refers to plant matter.

The term "biofuel" and grammatical variants thereof, refers to a fuel derived directly or indirectly from biological, organic matter, used as an energy source (e.g., to produce heat or power).

The term "biochemical" and grammatical variants thereof, refers to a chemical product or intermediate derived directly or indirectly from a biological process.

The term "biorefinery" and grammatical variants thereof (e.g., "biorefining"), refers to a facility that integrates biomass conversion processes and equipment to produce biofuels and/or biochemicals from biomass. The equipment for use in the biorefinery systems of the present disclosure includes any suitable equipment for performing the methods described. Such equipment includes, mechanical size-reduction equipment (e.g., grinders, millers), transport conduits (e.g., hoses, pipes, conveyers, and other fluid conduits), separation equipment (e.g., decanters, centrifuges, distillation columns, molecular sieves), non-reactor tanks, seed train tanks, bioreactors, water filtration equipment, filtration equipment (e.g., belt filters, vacuum belt filter, filter press), concentration equipment (e.g., evaporators, vapor-compression evaporation equipment, molecular sieves), steam generators, heat exchangers, pumps, compressors, boilers, water purification systems (e.g., reverse osmosis, filtration, deionizers, aerobic and anaerobic digesters), storage tanks, and other equipment suitable for use in performing the methods described, or combination(s) thereof.

The terms "transesterification," "transesterified," and grammatical variants thereof, refers to the process of exchanging an alkoxy group of an ester compound with another alcohol.

The term "genetically modified" and grammatical variants thereof, refers to a microorganism (e.g., a bacteria) containing genetic material that has been manipulated in a laboratory through techniques of genetic engineering to produce one or more desired characteristics.

The term "sugar converting microorganism" or "SC microorganism" refers to a microorganism capable of converting sugars to biofuels.

The term "toxin converting microorganism" or "TC microorganism" refers to a microorganism capable of removing one or more toxins from a stream, by conversion or adsorption.

The embodiments described may include a series of concurrent, countercurrent, and single pass processes for the conversion of lignocellulosic material into biofuels and/or biochemicals.

Preparation

Raw material biomass including lignocellulosic material(s) is milled or cut into pieces to an appropriate, desired size. In some instances, such size may be about 1 centimeters (cm) to about 10 cm in length, such as about 3 cm to about 7 cm in length, regardless of the shape of the milled material. The raw material biomass may be one or more of a variety of plant matter, such as, for example, corn stover, switchgrass, wheat straw, other plant matter or combination(s) thereof. The milled biomass is transported for feed preparation. In some embodiments, the milled biomass may have a moisture content suitable for feed preparation, such as about 10% to about 40% moisture by weight of the milled biomass, such as about 20% moisture by weight of the milled biomass. Depending, for example, on the moisture content of the milled biomass, which may stem from the type of biomass and the storage conditions, the biomass may be slurried or blended (e.g., made into a thin and viscous fluid). In some embodiments, the milled biomass may be slurried in an amount of from about 0% (not slurried) to about 30% by weight of the milled biomass, such as about 20% to about 25% by weight of the milled biomass, thereby forming a prepared feed. In some embodiments, the biomass may be slurried with water. Alternatively, the now-milled biomass may be conveyed directly as a solid feed such that the milled biomass is used as the prepared feed.

Pretreatment

The conversion of lignocellulosic materials includes a pretreatment, which includes deconstruction of the prepared feed into its primary components of hemicellulose, cellulose, and lignin. Pretreatment may include: physical, physiochemical, chemical, or biological methods. Examples include, mechanical pretreatments (e.g., grinding, milling, etc.), hot water or steam (explosion) pretreatments, ammonia fiber expansion (AFEX) pretreatments, acid or alkaline pretreatments (e.g., sulfuric acid, sodium hydroxide), oxidizing agent pretreatments (e.g., hydrogen peroxide, employing ozonolysis), sulfite pulping, fungal pretreatments, enzymatic pretreatments, solvent-assisted extraction, or combination(s) thereof.

During pretreatment, hemicellulose may be broken down into sugar species including pentose and/or hexose monosaccharides; typically hemicellulose contains more pentose sugars than hexose sugars. Pentose sugars are monosaccharides including five atoms of carbon, such as xylose, rhamnose, and arabinose. Hexoses are monosaccharides including six atoms of carbon, such as glucose, galactose, and mannose. The relative amounts of pentose and hexose sugars released from hemicellulose depends on the source of lignocellulosic biomass and the employed pretreatment technologies. In some embodiments, the yield of pentose monosaccharides from dry biomass feed may be about 10% to about 30%, such as about 20% to about 25% by weight of the biomass. The pretreatment technologies can be selected based on the treatment's ability to release each sugar component. Pretreatment produces a pretreatment effluent that may include aqueous solution of monosaccharides, cellulose, lignin, and/or a portion of the hemicellulose including oligosaccharides that were not broken down during pretreatment.

In some embodiments, condensed water is removed from the pretreatment system and may contain about 1 to 2 wt % organic impurities. The condensed water may be sent to an anaerobic and/or aerobic digester for treatment. The treated water therefrom may thereafter be reused and/or filtered for other uses. In some embodiments, the condensed water that has been treated and/or filtered may be reused within the biological conversion processes. Further, in some instances, the anaerobic digester may be used to produce and harness biogas (including mostly methane) and an organic-rich, high-solid content (sludge).

Other by-products may additionally be re leased during hemicellulose pretreatment such as, for example, organic acids (e.g., formic acid, acetic acid, carboxylic acid, furoic acid), furan compounds (e.g., furan, furfurals, hydroxymethylfurfuals), and combinations thereof. Hemicellulose pretreatment may be achieved by any of the suitable methods described above, and in some embodiments, is achieved using an acid pretreatment (e.g., by employing a mild acid reaction using, for example, a dilute sulfuric acid solution). The acid pretreatment may be performed with loadings of about 5 milligrams (mg) of acid per gram (g) of biomass to about 30 mg of acid per g of biomass, such as about 10 mg, about 15 mg, about 20 mg, about 25 mg, or about 30 mg of acid per g of biomass, or from about 5 mg to about 30 mg, from about 10 mg to about 20 mg, or from about 10 mg to about 15 mg of acid per gram of biomass. The concentration of pentose and hexose, as well as the type and concentration of by-products may depend on a number of factors including, the type of biomass being pretreated, the pretreatment method selected, the conditions related to the pretreatment method, and combinations of these or other factors.

Hydrolysis System

The pretreatment effluent may include pentose and hexose monosaccharides, lignin, cellulose, and sugar oligomers that were not broken down during pretreatment. The pretreatment effluent may be further hydrolyzed to release remaining sugars as monosaccharides, which may be accomplished by any suitable method, including methods described for pretreatment, and, in some embodiments, may be achieved using enzymatic hydrolysis. Enzymatic hydrolysis may be performed in the presence of enzymes derived from various organisms, including bacteria or fungi. The enzymes may be purchased commercially and/or manufactured directly at a biorefining site (at a location that the biological conversion of biomass containing lignocellulosic materials is performed).

In some embodiments, the enzyme used for the hydrolysis portion is prepared on-site at the biorefinery location and is fed to the hydrolysis system for performance of the hydrolysis portion of the methods and systems described. One or more feeds may provide various nutrients (e.g., sugars, vitamins, and salts) to support the production of the enzyme. Alternatively or additionally, the enzymes may be produced at another location or otherwise outside of the flow of the biological conversion process and thereafter fed into the hydrolysis system, such as in fermentation equipment, appropriate laboratory, or purchased commercially, without departing from the scope of the present disclosure.

Examples of suitable enzymes may include, one or more cellulases and/or hemicellulases that aid in the decomposition of cellulose. Such cellulases may include an endoglucanase, an exoglucanase, a β-glucosidase, or combination(s) thereof. Enzyme loadings can vary depending on the enzyme mix, but may be from about 5 mg of enzyme per g of cellulose to about 25 mg of enzyme per g of cellulose, such as about 5 mg, about 10 mg, about 15 mg, about 20 mg, or about 25 mg, of enzyme per g of cellulose, or from about 5 mg to about 25 mg, from about 10 mg to about 20 mg, or from about 10 mg to about 15 mg of enzyme per g of cellulose. Hydrolysis may convert at least a portion of the cellulose and remaining hemicellulose to hexose monosaccharides, such as glucose, and may also yield additional pentose monosaccharides (e.g., in addition to those obtained from the breakdown of the hemicellulose). A typical yield of hexose monosaccharides from dry biomass feed may be about 25% to about 45% by weight, such as about 30% to about 40% by weight. Typically the lignocellulosic pentose lean stream contains few pentose sugars, for example the lignocellulosic pentose lean stream may contain about 30 wt % or less, 25 wt % or less, 20 wt % or less, 15 wt % or less, 10 wt % or less, or 5 wt % or less of pentose sugars. Hydrolysis produces a hydrolysate that may include aqueous solution of monosaccharides, lignin and/or a portion of the cellulose or hemicellulose that was not broken down during hydrolysis.

Other by-products may additionally be released during hydrolysis of the lignocellulosic pentose lean stream such as, for example, organic acids (e.g., formic acid, acetic acid, carboxylic acid, furoic acid), furan compounds (e.g., furan, furfurals, hydroxymethylfurfuals), and combinations thereof.

Lignin Separation System

The hydrolysate may be sent to a lignin separation system for separation of a sugar-rich stream and a lignin-rich stream including the remaining solids, which are mostly lignin, but may include portions of cellulose or hemicellulose that were not broken down during pretreatment or hydrolysis. The separation may include any suitable method of separating the aqueous sugar-rich stream from the lignin-rich stream, such as depolymerization, filtration, centrifugation, or combination(s) thereof. In some embodiments, the insoluble lignin in the aqueous hydrolysate is removed by filtration (e.g., vacuum filtration, belt filtration). The filtration process removes all or substantially all lignin and insoluble solids in the hydrolysate producing the lignin-rich stream, while retaining about 80 wt % or greater, such as about 90 wt % or greater, about 95 wt % or greater, about 98 wt % or greater, or about 99 wt % or greater of the sugars in the liquid phase sugar-rich stream that is substantially lignin-free, based on the total weight of sugars in the sugar-rich stream. During filtration processes, water may be injected to facilitate filtration and removal of lignin and other insoluble solids. Water may be obtained from the anaerobic/aerobic digestion process of waste water and subsequent water filtration of other processes.

The lignin-rich stream may include a moisture content, such as about 20 wt % to about 40 wt % moisture content, and can be transported to a boiler/steam generator. The steam generator may, for example, be used to generate heat to produce high pressure, superheated steam. The steam created by the steam generator may be used to satisfy the steam demands of the biological conversion processes, such as, for example, enzyme production, ion exchange bed regeneration (e.g., the purification system), sterilization needs (e.g., sterilization of bioreactors including seed trains and aerobic fermentation), or combination(s) thereof. Excess high pressure superheated steam may be sent to a turbo expander (or expansion turbine) equipped, for example, with an electrical generator to produce electricity which may thereafter be used to supply the electrical demands of the biological conversion processes. Excess power is exported to support other electrical needs within the biorefinery and/or outside of the biorefinery, as appropriate. In another embodiment, the moisture content in the lignin-rich stream can be lowered by drying and the lignin repurposed. For example, the dried lignin may be sold as a source of revenue or used as process fuel in the bioconversion systems and processes. Thus, the biological conversion platform may recycle resources to provide integrated fuel, steam, and electrical needs.

Concentration

The sugar-rich stream, which is now lignin-free or substantially lignin-free typically has a relatively low concentration of monosaccharides, such as from about 5% to about 20%, or about 10% to about 15%, by weight of the sugar-rich stream.

In some embodiments, the sugar-rich stream may be concentrated to facilitate production of biofuel and/or biochemicals, such as to reduce equipment size (e.g., smaller bioreactors) and facilitate processing. Concentration may be achieved by any suitable methods including, vapor compression evaporation (e.g., mechanical vapor compression or thermocompression), membrane filtration (e.g., ultrafiltration membranes), reverse osmosis, or combination(s) thereof. Concentration of the sugar-rich stream yields a sugar content of the concentrated effluent of about 30% to about 60% by weight of the concentrated effluent (product of concentration of a lignin-free stream), such as about 40% to about 50% by weight of the concentrated effluent.

Excess water may be removed during concentration and be sent to anaerobic and/or aerobic digestion for further processing and reuse in the biological conversion processes.

Purification System

At various locations within or along the biorefinery, a purification system may be included because the pretreatment effluent, the sugar-rich stream, and/or the concentrated effluent may include a wide variety of compounds, such as water, monosaccharides, and various produced byproducts. Some byproducts may be harmful or toxic to the SC microorganism (e.g., a genetically modified E. coli) used in conversion of monosaccharides into biofuel or biochemical products. Additionally, some byproducts might not be directly harmful or toxic to the SC microorganism, but may inhibit the bioconversion processes.

Furthermore, during the concentration of a sugar-rich stream, other harmful byproducts (e.g., the toxins/inhibitors described above) may also be concentrated, which can effectively render the SC microorganism used later in the biological conversion process ineffective. Additionally, the toxins or inhibitors may build up in a fed-batch reactor decreasing the efficiency of the bioconversion of sugars into fuels and chemicals.

Accordingly, one or more of the various streams may be purified prior to continuing in a bioconversion process. The purification may remove byproducts and other undesirable impurities including toxins and inhibitors. Purification may be achieved by the use of a biological guard bed alone or in combination with other suitable methods including physical, chemical, or biochemical purification procedures, such as the use of chemical reducing agents, adsorption beds (e.g., ion exchange resin beds, activated carbon beds), liquid-liquid extraction, reactive extraction, catalytic distillation, evaporation, filtration, membranes, or combination(s) thereof.

A biological guard bed may include one or more bioreactors or other suitable vessels, in series or parallel, such as stirred tanks or bubble columns. The one or more bioreactors may operate in batch, fed-batch, or continuous mode depending on process requirements. The biological guard bed also includes one or more TC microorganisms or subcellular materials for the bioconversion of toxins and inhibitors. A biological guard bed may include one or more TC microorganisms or subcellular materials and different biological guard beds may include different TC microorganism(s) or subcellular material(s). Furthermore, a guard bed bioreactor may include a plurality of TC microorganisms and/or subcellular materials. The selection and distribution of the TC microorganism per guard bed reactor may depend on process conditions including, flow rates, inhibitor concentrations, diversity of inhibitors, and the rate of conversion for individual inhibitors.

In at least one embodiment, the purification system removes about 30 wt % to about 100 wt % of carboxylic acids in a stream, such as about 30 wt % to about 80 wt %, about 40 wt % to about 60 wt %, or about 45 wt % to about 55 wt %, based on the total weight of carboxylic acids in the stream.

In at least one embodiment, the purification system removes about 30 wt% to about 100 wt % of furan compounds in a stream, such as about 30 wt % to about 80 wt %, about 40 wt % to about 60 wt %, or about 45 wt % to about 55 wt %, based on the total weight of furan compounds in the stream.

The one or more TC microorganisms or subcellular materials can be configured to digest or remove inhibitors and/or toxins, and the configuration may reduce or eliminate digestion or other consumption of the sugars present in a given stream. The TC microorganism(s) or subcellular material(s) may be grown in-situ, added continuously, or added based on concentrations of certain inhibitors or toxins. Furthermore, the TC microorganisms in a biological guard bed can be grown as dispersed in the solution (planktonic) or as attached to an abiotic surface/matrix (biofilm). Similarly, subcellular components of TC microorganisms, such as enzymes responsible for the actual conversion, can be soluble in the guard bed liquid or immobilized to specific polymers and materials. Additionally, a guard bed bioreactor may be capable of receiving other reactants or reagents, such as feeds or energy sources for the TC microorganism(s) or subcellular material(s), air, or oxygen. Carbon dioxide or other gases produced in a biological guard bed may be vented, such as when they reach a volume within the guard bed of about 10% to 30%, such as 15% to 25%, 18% to 22%, or 19% to 20% of the total volume of the guard bed and balanced by air that may be used in aerobic processes.

Few TC microorganisms are known to selectively degrade furans like hydroxymethylfurfural (HMF) and furfural or other toxic compounds, like phenolic compounds and organic acids. *Cupriavidus basilensis* and *Pseudomonas putida* have been reported as capable of degrading furans, and the genes for HMF utilization have been reported in few other bacterial genera.

Bioconversion to Fuels and/or Chemicals

A concentrated and/or purified sugar-rich stream may be fed into an aerobic bioreactor including a genetically modified bacteria, such as *E. coli*, that is initially grown (e.g., replicated in a series of batch reactors of a seed train) and used to metabolically convert the sugars into fatty acid. The combined sugar-rich stream and genetically modified bacteria stream is introduced into the bioreactor at an initial volume of about 10% to about 40% by volume of the bioreactor, such as about 20% to about 30% by volume of the bioreactor. The amount of a lignin-free stream that is added is determined by the desired sugar concentration of the SC microorganism used. The lignin-free stream may provide nutrients to continue the growth (replication) of the SC microorganisms.

The SC microorganism population in the bioreactor is monitored until the population concentration reaches a desired or a suitable level; generally, at the suitable concentration the SC microorganisms begin producing fatty acid. Upon reaching the desired level, additional sugars are introduced into the bioreactor to facilitate further production of fatty acid in the cells of the genetically modified SC microorganisms. The fermentation and biological conversion process of the embodiments described may be aerobic, with the SC microorganisms producing fatty acids within their cells and in the process releasing carbon dioxide ($CO_2$). Oxygen or air is pumped into the bioreactor to maintain aerobic respiration in the bioreactor, and in some embodiments, is sparged into the production bioreactor, such as from the bottom thereof. The $CO_2$ may be vented at a given concentration, such as at a concentration of about 10% to 30%, such as 15% to 25%, 18% to 22%, or 19% to 20% and the balance is air used in the aerobic process.

Any suitable genetically modified SC microorganism may be used in accordance with the methods and systems described. In some embodiments, the SC microorganism is genetically modified using modern, available molecular biology tools to enhance the SC microorganism's metabolism and physiology to improve the conversion of biomass monosaccharides into fatty acids, such as fatty acid esters (e.g., FAME or FAEE). An example of a suitable genetically modified SC microorganism for use in the embodiments described is genetically modified *E. coli* disclosed in U.S. Patent Publication No. 2017/0175152, incorporated by reference. Fatty acid-derived biofuels and biochemicals are viable, renewable, sustainable, and cost-effective alternatives to traditional fossil fuels. The pathway for fatty acid biosynthesis in bacteria, such as *E. coli*, generally is carried out by a type II fatty acid synthase (FAS) enzyme. FAS is a multi-enzyme protein that catalyzes fatty acid synthesis in the presence of an alcohol by one or more biological pathways, which can be harnessed to produce biofuels and/or biochemicals. Typically, the genetically modified *E. coli* (a SC microorganism) is susceptible to the presence of furans, e.g., HMF, furfurals, etc., and acids, such as formic acid, levulinic acid, etc. For instance, a furans concentration in excess of 800 ppm in the bioreactor is known to inhibit the bioconversion and adversely affect the genetically modified *E. coli*. Hence, control measures are needed to reduce the furans concentration to about 800 ppm or less in the bioreactors, such as about 700 ppm or less, about 600 ppm or less, or about 500 ppm or less.

The fatty acid is thereafter transesterified using one or more alcohols including methanol, ethanol, or combination(s) thereof. For example, the fatty acid may be transesterified using methanol to produce a fatty acid methyl ester (FAME) or ethanol to produce a fatty acid ethyl ester (FAEE). Methanol may be obtained commercially and introduced into the bioreactor. Ethanol may also be obtained commercially. Alternatively or additionally, ethanol may be produced in situ in the bioreactor through fermentation of sugar(s) in the bioreactor. In some embodiments, a combination of alcohols (e.g., a combination of methanol and ethanol) may be used in the bioreactor, resulting in a combination of fermented fatty acids. Typically, the concentration of alcohol included in the bioreactor may about 1 wt % to about 10 wt % based on the total weight of the sugar concentrated effluent described (e.g., a lignin-free stream fed to the reactor), such as about 3% to about 7% by weight of the sugar concentrated effluent. The alcohol may be injected into the one or more bioreactors by any suitable means, such as one or more injection points at the bottom thereof, the top thereof, other points along the axis of the bioreactor, or combination(s) thereof.

The systems and methods described may include one or more bioreactors. Such bioreactors may operate in batch, fed-batch, or continuous mode. The one or more bioreactors may be any suitable bioreactors including those using sparged stirred-tank reactors, bubble column reactors, or combination(s) thereof. Heat generated during the fermentation within a bioreactor may be removed by any suitable methods including, use of internal cooling lines, jacketed walls, loop around (external) cooling lines, and external refrigeration. In some embodiments of the present disclosure, the one or more bioreactors include internal cooling lines in combination with stirred tanks that are designed as a coil around the mixing impeller shaft to act as a draft tube to enhance liquid circulation and cooling. Moreover, one or more impellers of different types may be employed in the one or more bioreactors, such as axial impeller(s) or radial impeller(s). In some embodiments, greater than one and/or greater than one type of impeller may be used in the bioreactors described. In some embodiments, the one or more bioreactors may include a bubble column with internal cooling lines.

Product Recovery

When a batch reactor fills to substantial or complete capacity, the feed is stopped and the products recovered. The effluent from the bioreactor is sent to a recovery block where the organic hydrocarbon is removed from the aqueous stream using a series of decanter vessels and further purified, such as to a purification level of 99% by weight (wt %) or higher (e.g., about 99.5 wt %), with the balance being aqueous phase with impurities. Such purification may be achieved by any suitable methods including centrifugation, water washing, membranes, or combination(s) thereof. The now substantially empty bioreactors can be sterilized, typically with steam at high pressure, and then put back on stream. Consequently, there are reactors with different fill levels as a function of time on stream.

Various waste waters are obtained throughout the biological conversion process, including from the pretreatment, hydrolysis, concentration, product recovery, or other process(es). These waste waters can be reprocessed, such as by using an anaerobic and/or aerobic digester to remove organic impurities, including further coupling with water filtration methods. For example, the aqueous phase effluent from product recovery may be transported to an anaerobic and/or aerobic digester for further processing and reuse in the biological conversion processes. The anaerobic and/or aerobic digesters may be configured in the biological conversion processes to receive one or more of the waste waters (e.g., pretreatment water, condensation water, aqueous phases) generated during the process. Digested water may be further filtered and reused in the biological conversion processes, such as to the filter press for lignin separation, the feed preparation, and/or steam generation for other process(es). Various filtration methods may be used, such as ultrafiltration, nanofiltration, reverse osmosis, or combination(s) thereof. Through digestion and reuse of waste waters, as well as in other ways, the biological conversion systems and methods facilitate an integrated process that recycles certain elements for conservation of power and resources. In some embodiments, additional fresh water may also be introduced into the biological conversion processes of the present disclosure, as needed. In other embodiments, additional fresh water and/or recycled water may be introduced into the system to facilitate enzyme production, enzymatic hydrolysis, product recovery, or utility needs.

Biogas (e.g., gaseous fuel, methane, fermentation products) and sludge, an organic-rich slurry, generated in an anaerobic digester may be burned in a boiler to generate steam for turbines to produce power, which can be utilized in the biological conversion processes or in other processes requiring power. Further contributing to the integrated nature of the biological conversion systems and processes described. Also, an aerobic digester may be used to further decompose remaining organic species carried over from the anaerobic digester. Accordingly, the biological conversion processes of the present disclosure allow for heat, power, and steam integration.

Figure 1A:
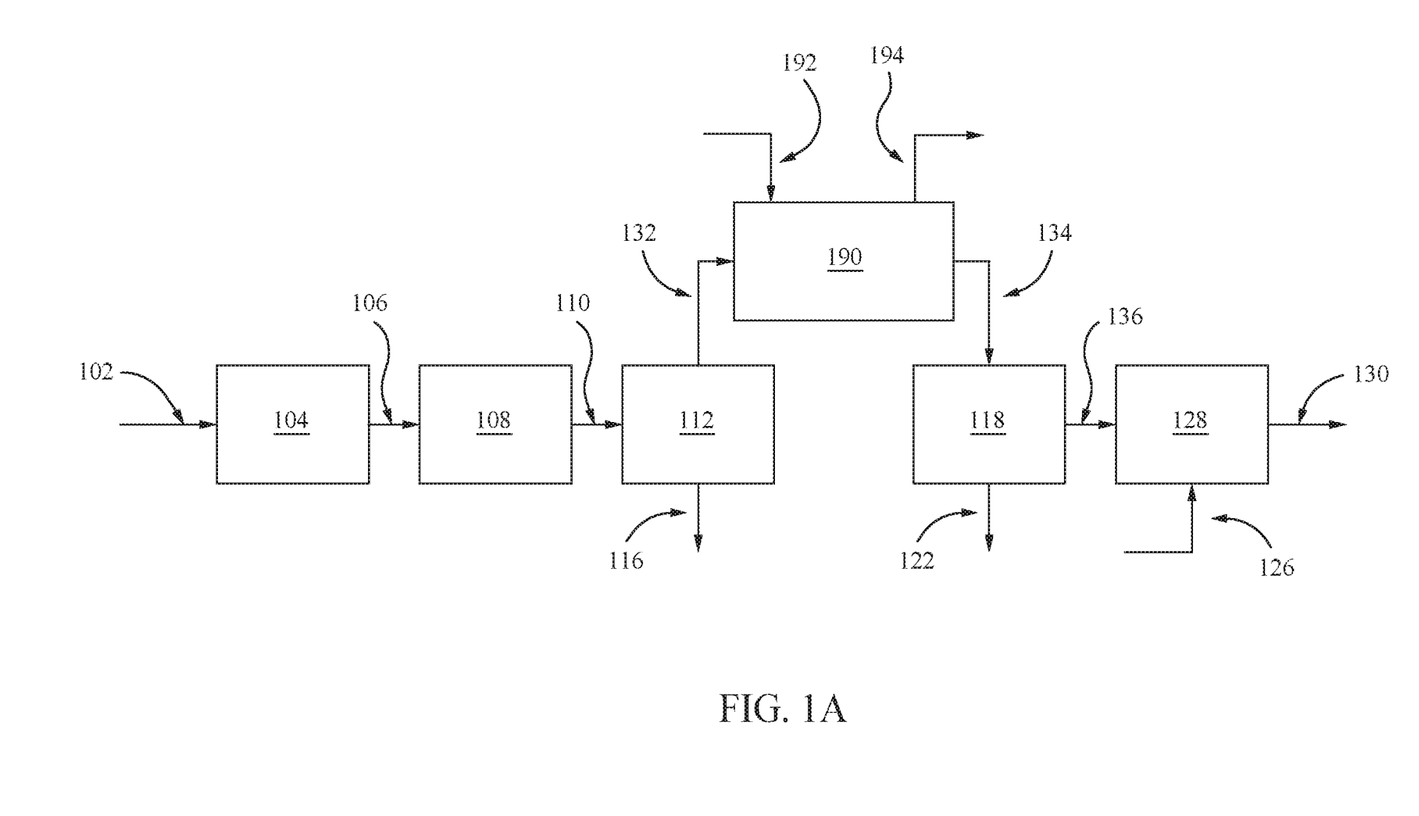
FIG. 1A depicts a schematic diagram of a system for bioconversion of lignocellulosic biomass to hydrocarbon fuel and/or other chemicals according to an embodiment.

Referring to FIG. 1A, FIG. 1A is a schematic diagram of a system for bioconversion of sugars obtained from lignocellulosic biomass to hydrocarbon fuels and/or chemicals. FIG. 1A shows a configuration where purification takes place after pre-treatment, hydrolysis, and lignin separation. Therefore, the purified feed contains an dilute sugar stream with substantially no solids including lignin, and reduced or eliminated toxins and/or inhibitors. The prepared feed 102 is introduced to pretreatment system 104, a deconstruction portion of the biological conversion system. In pretreatment system 104, the prepared feed 102 is deconstructed or broken down into its main constituent parts (hemicellulose, cellulose, and lignin) using one or more pretreatment methods, such as an acid pretreatment coupled with a steam (explosion) pretreatment.

The pretreatment effluent 106 including hemicellulose, cellulose, lignin, and released sugars is thereafter hydrolyzed in hydrolysis system 108 to produce a hydrolysate. The hydrolysate may include hexose and pentose monosaccharides, and solid matter including lignin, cellulosic materials that were not broken down in the hydrolysis system such as cellulose, hemicellulose, and oligosaccharides resistant to hydrolysis methods employed. The hydrolysate may be sent through line 110 to lignin separation system 112 where solid material is separated from aqueous sugars producing a lignin-free stream 132 and a lignin-rich stream removed via line 116.

As shown in FIG. 1A, the lignin-free stream may be sent through line 132 to purification system 190 for reduction or elimination of toxins and inhibitors through one or more biological guard beds. Purification system 190 may include one or more lines for the introduction of co-reactants, or reagents, such as air, or energy sources for the TC microorganism(s) or subcellular material(s), such as line 192. Additionally, purification system 190 may include one or more vent lines, such as vent line 194, to allow for efficient removal of gases, such as carbon dioxide, methane, or hydrogen produced in the purification process. The co-reactants or reagents used in purification of an unconcentrated sugar-rich stream might not be identical to reactants and/or reagents used in purification of a concentrated sugar-rich stream. Therefore, the composition of material vented through line 194 might not be the same when different sugar-rich streams are purified. Purification system 190 may include one or more bioreactors, which individually may include one or more TC microorganism(s) or subcellular material(s) to produce dilute purified sugar stream 134. A configuration where purification takes place previous to concentration may be advantageous where the TC microorganism(s) or subcellular material(s) used in the purification process show a slight selectivity towards sugars and therefore a lower sugar concentration may provide a kinetic rate that reduces sugar loss.

The dilute purified sugar stream may be concentrated in concentration system 118 and the concentrated effluent sent for bioconversion through line 136, with water removed through line 122. Removed water may be recycled for use in systems or processes including steam generation.

Concentrated purified sugar-rich stream may be sent to bioconversion system 128 through line 136. The bioconversion system may include one or more bioreactors, which may be fed-batch bioreactors, configured for the production of fuels and/or other chemicals from sugars produced from biomass. As aqueous sugars are added to a fed-batch reactor the SC microorganisms multiply and the combination of SC microorganism growth and addition of other materials fill the bioreactor. Initially, a quantity of SC microorganism can be introduced to the one or more bioreactors from a seed train, which may include another series of bioreactors designed to aid in the growth and replication of the SC microorganism. Typically the SC microorganism(s) and a sugar-rich stream are introduced to a bioreactor at an initial volume of about 10% to about 40% by volume of the bioreactor, or about 20% to about 30% by volume of the bioreactor. The bioconversion system may receive additional reactants, such as air and/or alcohol via sparge line 126. Air is used in the SC microorganisms' aerobic processes including the production of fatty-acids, and alcohols may be used by the SC microorganism to convert fatty-acids to fatty-acid esters. The one or more bioreactors may receive more of the sugar-rich stream, including pentose or hexose monosaccharides and as the time on stream increases, the volume of material within the reactor increases until the reactor is substantially or completely full. Once the reactor is substantially or completely full, the material is removed and the product(s) are recovered. The products, including fuels or chemicals are removed through product line 130.

Figure 1B:
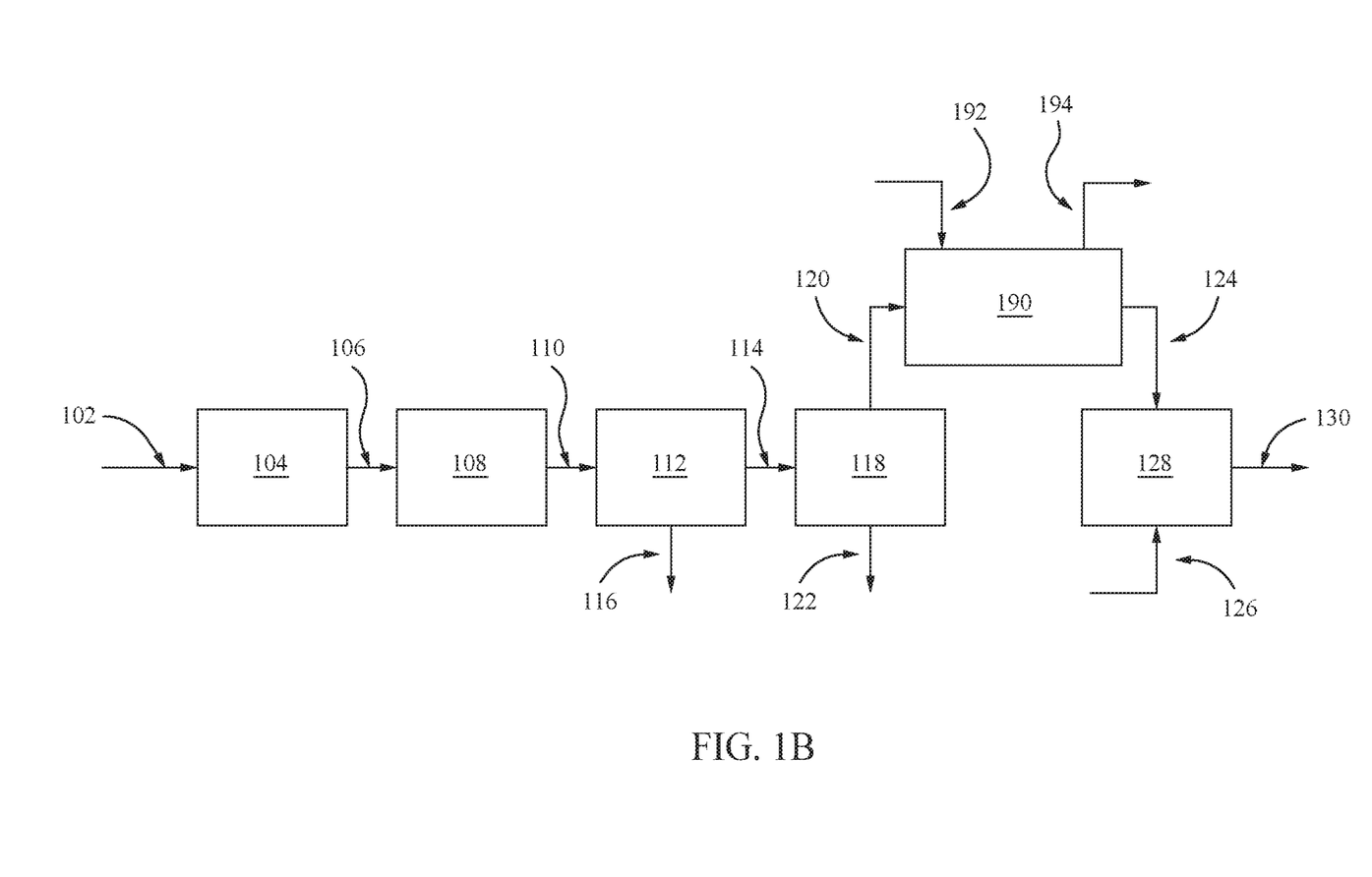
FIG. 1B depicts a schematic diagram of a system for bioconversion of lignocellulosic biomass to hydrocarbon fuel and/or other chemicals according to an embodiment.

Referring now to FIG. 1B, FIG. 1B is a schematic diagram of a system for bioconversion of sugars obtained from biomass to hydrocarbon fuel and/or chemicals similar to FIG. 1A, except that purification take place later in the process. FIG. 1B shows a configuration where purification takes place after pre-treatment, hydrolysis, lignin separation, and concentration. Therefore, the purified feed contains a concentrated sugar stream with substantially no solids including lignin, and reduced or eliminated toxins and/or inhibitors. Placement of the purification system upstream of bioconversion of sugars to fuels and/or chemicals may provide various advantages over previous methods, including increased efficiency in the bioconversion process and improved sugar availability. Additionally, including the purification near the end of the system allows for purification of by-products that may be created during upstream processes of the conversion of lignocellulosic biomass to fuels and/or chemicals.

As shown in FIG. 1B, the prepared feed 102 is introduced to pretreatment system 104, a deconstruction portion of the biological conversion system. In pretreatment system 104, the prepared feed 102 is deconstructed or broken down into its main constituent parts (hemicellulose, cellulose, and lignin) using one or more pretreatment methods, such as an acid pretreatment coupled with a steam (explosion) pretreatment.

The pretreatment effluent 106 including hemicellulose, cellulose, lignin, and released sugars is thereafter hydrolyzed in hydrolysis system 108 to produce a hydrolysate. The hydrolysate may include hexose and pentose monosaccharides, and solid matter including lignin, cellulosic materials that were not broken down in the hydrolysis system such as cellulose, hemicellulose, and oligosaccharides resistant to hydrolysis methods employed. The hydrolysate may be sent through line 110 to lignin separation system 112 where solid material is separated from aqueous sugars producing a sugar-rich stream 114 and a lignin-rich stream removed via line 116. The sugar-rich stream may be concentrated in concentration system 118 and the concentrated effluent sent for purification through line 120, with water removed through line 122. Removed water may be recycled for use in systems or processes including steam generation.

The concentrated effluent may be sent to purification system 190 through line 120 for reduction or elimination of toxins and inhibitors through one or more biological guard beds. Purification system 190 may include one or more lines for the introduction of co-reactants, or reagents, such as air, or energy sources for the TC microorganism(s) or subcellular material(s), such as line 192. Additionally, purification system 190 may include one or more vent lines 194 to allow for efficient removal of gases, such as carbon dioxide, methane, or hydrogen produced in the purification process. Purification system 190 may include one or more bioreactors, which individually may include one or more TC microorganism(s) or subcellular material(s) to produce concentrated and purified sugar-rich stream 124.

Concentrated and purified sugar-rich stream 124 may be sent to bioconversion system 128, which may include one or more bioreactors, which may be fed-batch bioreactors, configured for the production of fuels and/or chemicals from sugars produced from biomass. As aqueous sugars are added to a fed-batch reactor the SC microorganisms multiply and the combination of SC microorganism growth and addition of other materials fill the bioreactor. Initially, a quantity of SC microorganism can be introduced to the one or more bioreactors from a seed train, which may include another series of bioreactors designed to aid in the growth and replication of the SC microorganism. Typically the SC microorganism(s) and a sugar-rich stream are introduced to a bioreactor at an initial volume of about 10% to about 40% by volume of the bioreactor, or about 20% to about 30% by volume of the bioreactor. The bioconversion system may receive additional reactants, such as air and/or alcohol via sparge line 126. Air is used in the SC microorganisms' aerobic processes including the production of fatty-acids, and alcohols may be used by the SC microorganism to convert fatty-acids to fatty-acid esters. The one or more bioreactors may receive more of the sugar-rich stream, including pentose or hexose monosaccharides and as the time on stream increases the volume of material within the reactor increases until the reactor is substantially or completely full. Once the reactor is substantially or completely full, the material is removed and the product(s) are recovered. The products, including fuels and/or other chemicals are removed through product line 130.

Figure 1C:
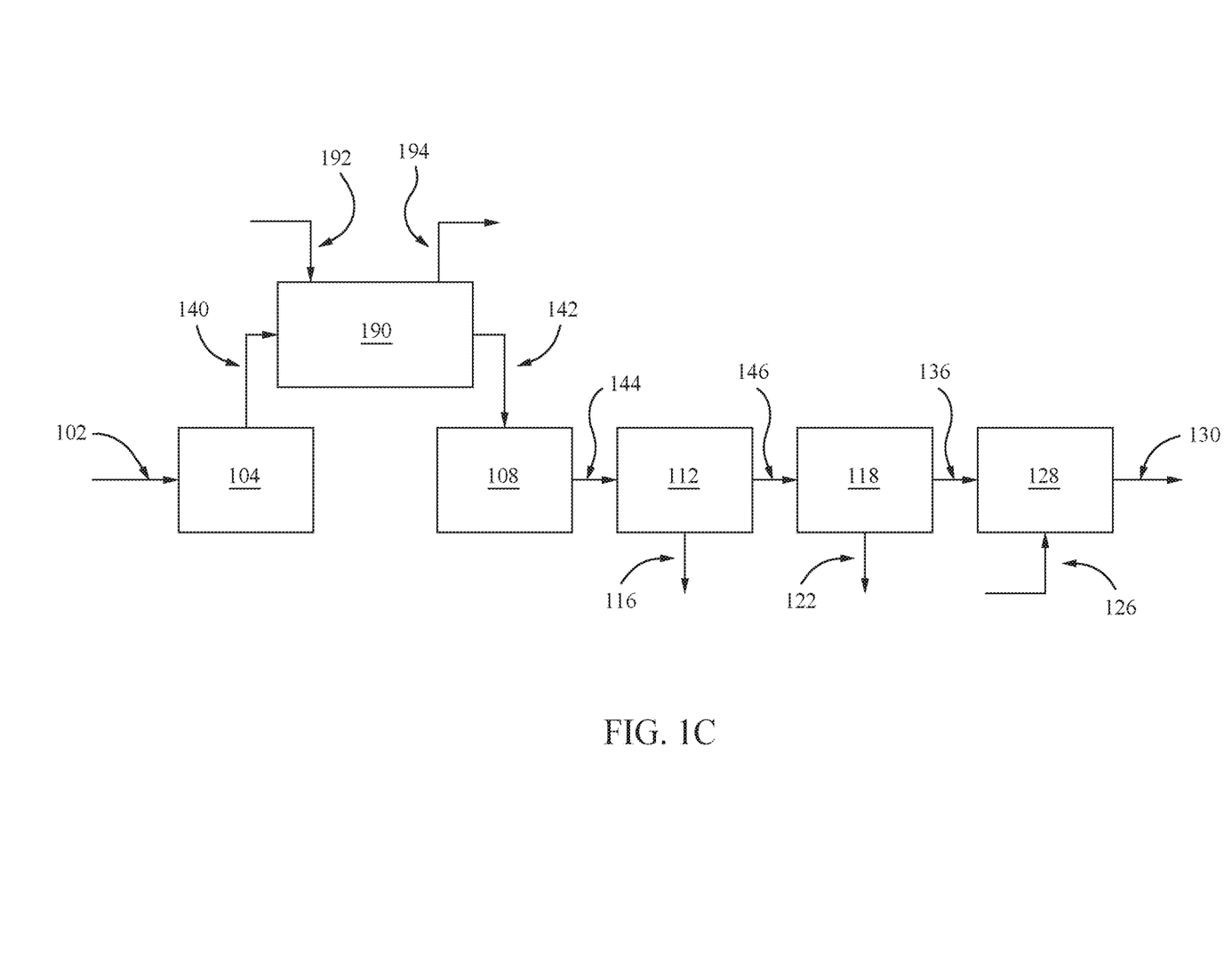
FIG. 1C depicts a schematic diagram of a system for bioconversion of lignocellulosic biomass to hydrocarbon fuel and/or other chemicals according to an embodiment.

Referring to FIG. 1C, FIG. 1C is a schematic diagram of a system for bioconversion of sugars obtained from lignocellulosic biomass to hydrocarbon fuels and/or chemicals similar to FIG. 1B, except that purification system 190 purifies the pretreatment effluent rather than a sugar-rich stream. FIG. 1C shows a configuration where purification takes place after pre-treatment. Therefore the purified feed contains sugars (from the breakdown of hemicellulose), and solids, including lignin, cellulose, and remaining hemicellulose. The purification product may have reduced or eliminated toxins and/or inhibitors. Similarly to FIG. 1B, the prepared feed 102 is introduced to pretreatment system 104, a deconstruction portion of the biological conversion system. In pretreatment system 104, the prepared feed 102 is deconstructed or broken down into its main constituent parts (hemicellulose, cellulose, and lignin) using one or more pretreatment methods, such as an acid pretreatment coupled with a steam (explosion) pretreatment.

As shown in FIG. 1C, the pretreatment effluent may be sent through line 140 to purification system 190 for reduction or elimination of toxins and inhibitors through one or more biological guard beds. Purification system 190 may include one or more lines for the introduction of co-reactants, or reagents, such as air, or energy sources for the TC microorganism(s) or subcellular material(s), such as line 192. Additionally, purification system 190 may include one or more vent lines, such as vent line 194, to allow for efficient removal of gases, such as carbon dioxide, methane, or hydrogen produced in the purification process. The co-reactants or reagents used in purification of pre-treatment effluent might not be similar to reactants and reagents use in purification of sugar-rich streams. Therefore, the composition of material vented through line 194 might not be the same as when different sugar-rich streams are purified. Purification system 190 may include one or more bioreactors, which individually may include one or more TC microorganism(s) or subcellular material(s) to produce purified pre-treatment effluent 142. A configuration where purification takes place previous to hydrolysis may be advantageous where toxins or inhibitors may affect the hydrolysis process, especially where the hydrolysis process is accomplished by microorganism(s) or subcellular material(s) and therefore purification of the pretreatment effluent may provide for a more efficient hydrolysis to sugars from biomass.

The purified pretreatment effluent 142 including solids such as hemicellulose, cellulose, lignin, and released sugars is thereafter hydrolyzed in hydrolysis system 108 to produce a hydrolysate. The hydrolysate may include hexose and pentose monosaccharides, and solid matter including lignin, cellulosic materials that were not broken down in the hydrolysis system such as cellulose, hemicellulose, and oligosaccharides resistant to hydrolysis methods employed. The purified hydrolysate may be sent through line 144 to lignin separation system 112 where solid material is separated from aqueous sugars producing a purified sugar-rich stream 134 and a lignin-rich stream removed via line 116.

The purified sugar-rich stream may be concentrated in concentration system 118 and the concentrated effluent sent for bioconversion through line 136, with water removed through line 122. Removed water may be recycled for use in systems or processes including steam generation.

Concentrated purified sugar-rich stream may be sent to bioconversion system 128 through line 136. The bioconversion system may include one or more bioreactors, which may be fed-batch bioreactors, configured for the production of fuels and/or chemicals from sugars produced from biomass. As aqueous sugars are added to a fed-batch reactor the SC microorganisms multiply and the combination of SC microorganism growth and addition of other materials fill the bioreactor. Initially, a quantity of SC microorganism can be introduced to the one or more bioreactors from a seed train, which may include another series of bioreactors designed to aid in the growth and replication of the SC microorganism. Typically the SC microorganism(s) and a sugar-rich stream are introduced to a bioreactor at an initial volume of about 10% to about 40% by volume of the bioreactor, or about 20% to about 30% by volume of the bioreactor. The bioconversion system may receive additional reactants, such as air and/or alcohol via sparge line 126. Air is used in the SC microorganisms' aerobic processes including the production of fatty-acids, and alcohols may be used by the SC microorganism to convert fatty-acids to fatty-acid esters. The one or more bioreactors may receive more of the sugar-rich stream, including pentose or hexose monosaccharides and as the time on stream increases the volume of material within the reactor increases until the reactor is full. Once the reactor is full, the material is removed and the product(s) are recovered. The Products, including fuels or chemicals are removed through product line 130.

FIGS. 1A through 1C demonstrate that the purification system (a biological guard bed) may be included at various points in the systems and processes used for conversion of biomass to fuels and/or other chemicals. In some embodiments, the purification system is included at two or more points in the processes and systems described, such as a purification system before hydrolysis for the removal of certain toxins and/or inhibitors in addition to a purification system located after concentration before bioconversion of sugars to fuels and/or chemicals. Additionally, the purification system may be included at any suitable point or multiple points in the processes and systems described for the production of fuels and/or chemicals from biomass.

EMBODIMENTS

Clause 1. A process for producing hydrocarbon fuels from lignocellulosic biomass, the process comprising:
introducing biomass to a pretreatment system forming a pretreatment effluent;
introducing the pretreatment effluent to a hydrolysis system forming a hydrolysate;
introducing the hydrolysate to a lignin separation system forming a sugar-rich stream and a lignin-rich stream;
introducing the sugar-rich stream to a purification system comprising at least one toxin converting microorganism or subcellular material to form a purified sugar-rich stream; and
introducing the purified sugar-rich stream and one or more sugar converting microorganisms to a bioreactor configured to produce hydrocarbon fuels.

Clause 2. The process of clause 1, wherein the purification system comprises a subcellular material comprising an enzyme.

Clause 3. The process of clause 1, wherein the purification system comprises a biofilm comprising the toxin converting microorganism.

Clause 4. The process of any of clauses 1 to 3, wherein the purification system removes about 40 wt % to about 60 wt % of carboxylic acids from the sugar-rich stream, based on the total weight of carboxylic acids in the sugar-rich stream.

Clause 5. The process of any of clauses 1 to 3 wherein the purification system removes about 40 wt % to about 60 wt % of furan compounds from the sugar-rich stream, based on the total weight of furan compounds in the sugar-rich stream.

Clause 6. The process of any of clauses 1 to 5, further comprising concentrating the sugar-rich stream to form a concentrated sugar-rich stream having a sugar concentration of 40 wt % to 60 wt % , based on the total weight of the concentrated purified sugar-rich stream.

Clause 7. The process of any of clauses 1 to 5, further comprising concentrating the purified sugar-rich stream to form a concentrated sugar-rich stream having a sugar concentration of 40 wt % to 60 wt %, based on the total weight of the concentrated purified sugar-rich stream.

Clause 8. The process of any of clauses 1 to 7, further comprising recovering at least one of fatty acid methyl ester or fatty acid ethyl ester from the bioreactor.

Clause 9. A process for producing hydrocarbon fuels from lignocellulosic biomass, the process comprising:
  introducing biomass to a pretreatment system forming a pretreatment effluent;
  introducing the pretreatment effluent to a purification system comprising at least one toxin converting microorganism or subcellular material to form a purified pretreatment stream;
  introducing the purified pretreatment stream to a hydrolysis system forming a purified hydrolysate;
  introducing the purified hydrolysate to a lignin separation system forming a purified sugar-rich stream and a lignin-rich stream; and
    introducing the purified sugar-rich stream and one or more sugar converting microorganisms to a bioreactor configured to produce hydrocarbon fuels.

Clause 10. The process of clause 9, wherein the purification system comprises a subcellular material comprising an enzyme.

Clause 11. The process of any of clauses 9 to 10, wherein the purification system removes about 40 wt % to about 60 wt % of carboxylic acids from the sugar-rich stream, based on the total weight of carboxylic acids in the sugar-rich stream.

Clause 12. The process of any of clauses 9 to 11, wherein the purification system removes about 40 wt % to about 60 wt % of furan compounds from the sugar-rich stream, based on the total weight of furan compounds in the sugar-rich stream.

Clause 13. The process of any of clauses 9 to 12, further comprising concentrating the purified sugar-rich stream to form a concentrated sugar-rich stream having a sugar concentration of 40 wt % to 60 wt %, based on the total weight of the concentrated purified sugar-rich stream.

Clause 14. The process of any of clauses 9 to 13, further comprising recovering at least one of fatty acid methyl ester or fatty acid ethyl ester from the bioreactor.

Clause 15. A system for production of hydrocarbon fuels, the system comprising:
  a pretreatment system configured to treat lignocellulosic biomass;
  a hydrolysis system coupled with to the pretreatment system;
  a lignin separation system coupled with to the hydrolysis system;
  at purification system coupled with to the lignin separation system; and
  at least one bioreactor coupled with to the purification system.

Clause 16. The system of clause 15, further comprising a concentration system coupled to the lignin separation system and the at least one bioreactor.

Clause 17. The system of clause 15, further comprising a concentration system coupled to the hydrolysis system and the purification system.

Clause 18. the system of any of clauses 15 to 17, wherein the lignin separation system is configured to separate solids from liquids to form a sugar-rich stream and a lignin-rich stream.

Clause 19. The system of any of clauses 15 to 18, further comprising a plurality of bioreactors coupled with the first separation system.

Clause 20. The system of any of clauses 15 to 19 wherein the lignocellulosic biomass is derived from at least one of: corn stover, switchgrass, or wheat straw.

Clause 21. The system of any of clauses 15 to 20, further comprising a sparge line coupled with the bioreactor and configured to deliver at least one of air, oxygen, methanol, or ethanol to the at least one bioreactor.

Clause 22. A system for production of hydrocarbon fuels, the system comprising:
  a pretreatment system configured to treat lignocellulosic biomass;
  a purification system coupled with the pretreatment system;
  a hydrolysis system coupled with to the purification system;
  a lignin separation system coupled with to the hydrolysis system; and
  at least one bioreactor coupled with to the lignin separation system.

Clause 23. The system of clause 22, further comprising a concentration system coupled to the lignin separation system and the at least one bioreactor.

Clause 24. The system of any of clauses 22 to 23, further comprising a plurality of bioreactors coupled with the first separation system.

Clause 25. The system of any of clauses 22 to 24, wherein the lignocellulosic biomass is derived from at least one of: corn stover, switchgrass, or wheat straw.

Clause 26. The system of any of clauses 22 to 25, further comprising a sparge line coupled with the bioreactor and configured to deliver at least one of air, oxygen, methanol, or ethanol to the at least one bioreactor.

EXAMPLES

An example of the changes in pentose, hexose, and furans concentration for FIG. 1A is shown in Table 1 below for corn stover as the main lignocellulosic biomass source. The furans concentration exiting the pretreatment step 104 was greater than 1200 ppm, which was in excess of the allowable limit for the bioconversion. This level does not change after hydrolysis step 108 and solid separation step 112. After the purification system 190, the furans concentration dropped below 330 ppm, which was below the threshold of the bioconversion inhibitor concentration limit.

TABLE 1

Composition Change in Monosaccharides and Furans Before and After Biological Guard Beds configured as in FIG. 1A

| Species | Line 106 | Line 110 | Line 132 | Line 134 |
|---|---|---|---|---|
| C5, wt. % | 4.3% | 4.2% | 4.4% | 4.4% |
| C6, wt. % | 1.2% | 7.1% | 7.5% | 7.4% |
| Furans, ppm | 1210 | 1191 | 1250 | 326 |

Overall, it has been found that purification with TC microorganism(s) or subcellular material(s) increases efficiency and reduces costs in the production of hydrocarbon fuels and other chemicals from biological sources including lignocellulosic biomass. The efficiencies created by the purification with TC microorganism(s) or subcellular material(s) may include fewer beds or reactors in purification systems, more efficient SC microorganisms for the bioconversion to fuels and/or chemicals, increased purification system capacity at similar costs, flexibility in acceptance of various feed streams, or flexibility in types of toxins and inhibitors removed. Additionally, a purification system that includes TC microorganism(s) or subcellular material(s) may have improved reduction of toxins or inhibitors over prior processes and systems. Additionally, the development of SC microorganisms useful in bioconversion of sugars to fuels and/or chemicals is time consuming and labor intensive and including resistance to toxins and/or inhibitors increases the time and labor required. Also, the upstream biological purification allows for more efficient development of SC microorganisms capable of efficiently producing fuels and chemicals from biomass, including lignocellulosic biomass.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of this disclosure, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All documents described herein are incorporated by reference herein, including any priority documents and/or testing procedures to the extent they are not inconsistent with this text. As is apparent from the foregoing general description and the specific embodiments, while forms of this disclosure have been illustrated and described, various modifications can be made without departing from the spirit and scope of this disclosure. Accordingly, it is not intended that this disclosure be limited thereby. Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

While this disclosure has been described with respect to a number of embodiments and examples, those skilled in the art, having benefit of this disclosure, will appreciate that other embodiments can be devised which do not depart from the scope and spirit of this disclosure.

What is claimed is:

1. A process for producing hydrocarbon fuel from lignocellulosic biomass, the process comprising:
    introducing biomass to a pretreatment system forming a pretreatment effluent;
    introducing the pretreatment effluent to a hydrolysis system forming a hydrolysate;
    introducing the hydrolysate to a lignin separation system to form a sugar-rich stream and a lignin-rich stream;
    introducing the sugar-rich stream to a purification system comprising at least one toxin converting microorganism or subcellular material from toxin-converting microorganisms to form a purified sugar-rich stream;
    introducing the purified sugar rich stream into a bioreactor comprising a sugar converting microorganism;
    introducing at least two different alcohols from a source apart from the purified sugar-rich stream into the bioreactor to form a purified sugar-rich stream with at least two different alcohols;
    and
    producing at least two different hydrocarbon fuels through transesterification reactions occurring on the purified sugar-rich stream with at least two different alcohols in the bioreactor by the sugar converting microorganism.

2. The process of claim 1, wherein the purification system comprises a subcellular material comprising an enzyme.

3. The process of claim 1, wherein the purification system comprises a biofilm comprising the toxin converting microorganism.

4. The process of claim 1, wherein the purification system removes about 40 wt % to about 60 wt % of carboxylic acids from the sugar-rich stream, based on the total weight of carboxylic acids in the sugar-rich stream.

5. The process of claim 1, wherein the purification system removes about 40 wt % to about 60 wt % of furan compounds from the sugar-rich stream, based on the total weight of furan compounds in the sugar-rich stream.

6. The process of claim 1, further comprising concentrating the sugar-rich stream to form a concentrated sugar-rich stream having a sugar concentration of 40 wt % to 60 wt %, based on the total weight of the concentrated sugar-rich stream.

7. The process of claim 1, further comprising concentrating the purified sugar-rich stream to form a concentrated purified sugar-rich stream having a sugar concentration of 40 wt % to 60 wt %, based on the total weight of the concentrated purified sugar-rich stream.

8. The process of claim 1, wherein the fuel is a fatty acid-derived biofuel and the process further comprises recovering at least one of fatty acid methyl ester or fatty acid ethyl ester from the bioreactor.

9. The process of claim 1, further comprising introducing water to the lignin separation system, wherein the water is obtained from an anaerobic digestion process of waste water.

10. The process of claim 9, wherein the anaerobic digestion process of waste water includes removing organic impurities, and wherein the anaerobic digestion is followed by waste water filtration.

11. The process of claim 9, further comprising introducing the lignin-rich stream to a steam generator to produce steam.

12. The process of claim 11, further comprising producing electricity by introducing the steam to an expander comprising an electrical generator.

13. The process of claim 1, wherein the purification system comprises at least one toxin converting microorganism configured to selectively degrade hydroxymethylfurfural and furfural.

14. The process of claim 1, wherein the two different alcohols are ethanol and methanol, and wherein the two different hydrocarbon fuels are fatty acid ethyl ester and fatty acid methyl ester.

15. The process of claim 10, wherein the anaerobic digestion process produces a biogas and an organic-rich sludge, the biogas and the organic-rich sludge burned in a boiler to generate steam.

16. The process of claim 1, wherein the sugar converting microorganism is configured to form fatty acid and transesterify the fatty acid to form one or more fatty acid esters.

17. The process of claim 1, wherein the fuel has a furan content of about 500 ppm or less.

18. The process of claim 1, wherein the bioreactor has a concentration of alcohol of about 1 wt % to about 10 wt % based on a total weight of the purified sugar-rich stream.

19. A process for producing hydrocarbon fuel from lignocellulosic biomass, the process comprising:
 introducing biomass to a pretreatment system forming a pretreatment effluent;
 introducing the pretreatment effluent to a hydrolysis system forming a hydrolysate;
 introducing the hydrolysate to a lignin separation system to form a sugar-rich stream and a lignin-rich stream;
 introducing the sugar-rich stream to a purification system comprising a toxin converting microorganism or subcellular material from a toxin-converting microorganism to form a purified sugar-rich stream;
 introducing the purified sugar-rich stream into a bioreactor;
 introducing at least two different alcohols from a source apart from the purified sugar-rich stream into the bioreactor to form a purified sugar-rich stream with at least two different alcohols;
 introducing a sugar converting microorganism configured to produce fatty acid esters into the bioreactor; and
 producing at least two different hydrocarbon fuels through transesterification reactions occurring on the purified sugar-rich stream with at least two different alcohols in the bioreactor by the sugar converting microorganism, wherein the at least two different hydrocarbon fuels comprise the fatty acid esters.

20. The process of claim 19, wherein the at least two different alcohols are methanol and ethanol.

* * * * *